United States Patent [19]

Dean et al.

[11] Patent Number: 5,153,192
[45] Date of Patent: Oct. 6, 1992

[54] THIOPHENE SULFONAMIDES USEFUL AS CARBONIC ANHYDRASE INHIBITORS

[75] Inventors: Thomas R. Dean, Weatherford; Hwang-Hsing Chen; Jesse A. May, both of Fort Worth, all of Tex.

[73] Assignee: Alcon Laboratories, Inc., Fort Worth, Tex.

[21] Appl. No.: 618,765

[22] Filed: Nov. 27, 1990

Related U.S. Application Data

[63] Continuation-in-part of Ser. No. 506,730, Apr. 9, 1990, abandoned.

[51] Int. Cl.$^5$ .................. C07D 513/04; A61K 31/54
[52] U.S. Cl. .................................. 514/226.5; 544/48
[58] Field of Search ............... 544/48; 514/226.5, 211, 514/373; 540/552; 548/209

[56] References Cited

U.S. PATENT DOCUMENTS

| | | | |
|---|---|---|---|
| 4,731,368 | 3/1988 | Hoffman, Jr. et al. | 514/301 |
| 4,746,745 | 5/1988 | Maren | 548/139 |
| 4,797,413 | 1/1989 | Baldwin et al. | 514/432 |
| 4,847,289 | 7/1989 | Baldwin et al. | 514/445 |

FOREIGN PATENT DOCUMENTS 661731 4/1963 Canada .
1516024 6/1978 United Kingdom .

OTHER PUBLICATIONS

"The Reactions of Some Thiophene Sulfonyl Derivatives," Cremyln et al., *Phosphorus and Sulfur*, vol. 10, pp. 111-119, 1981.
"Studien in der Thiophenreihe. XXIV.$^2$ Uber Nitrothiophene and Thiophensulfochloride," Steinkopf et al., *Justus Liebigs Analen Der Chemie*, vol. 501, pp. 174-186, 1933.
"Heterocyclic Disulphonamides and Their Diuretic Properties," deStevens et al., *Journal of Medicinal and Pharmaceutical Chemistry*, vol. 1(6), pp. 565-576, 1959.

*Primary Examiner*—John M. Ford
*Attorney, Agent, or Firm*—James Arno; Sally S. Yeager

[57] ABSTRACT

Thiophene sulfonamides and pharmaceutical compositions containing the compounds useful in controlling intraocular pressure are disclosed. Methods for controlling intraocular pressure through administration of the compositions are also disclosed.

11 Claims, No Drawings

THIOPHENE SULFONAMIDES USEFUL AS CARBONIC ANHYDRASE INHIBITORS

This is a continuation-in-part of U.S. Ser. No. 07/506,730, filed Apr. 9, 1990, now abandoned.

FIELD OF THE INVENTION

The present invention relates to new thiophene sulfonamides useful in lowering and controlling intraocular pressure. In particular this invention is directed to the (+) isomer of 3,4-dihydro-4-ethylamino-2-methyl-4H-thieno[3,2-e]-1,2-thiazine-6-sulfonamide-1,1-dioxide.

BACKGROUND OF THE INVENTION

Glaucoma is a disease of the eye which is characterized by a progressive loss of visual field due to irreversible damage to the optic nerve to the point where if untreated can result in total blindness. This loss of visual field, in one form of primary open angle glaucoma, or POAG, is associated with a sustained increase in the intraocular pressure (IOP) of the diseased eye. Moreover, elevated intraocular pressure without visual field loss is thought to be indicative of the early stages of this form of POAG.

There are a number of therapies that target reducing the elevated IOP associated with this form of POAG. The most common feature the topical administration of a beta adrenergic antagonist or a muscarinic agonist. These treatments while effective in lowering IOP can also produce significant undesirable side effects.

Another less common treatment for this form of POAG is the systemic administration of carbonic anhydrase inhibitors. However, these drugs also can bring about unwanted side effects, such as nausea, dyspepsia, fatigue, and metabolic acidosis.

U.S. Pat. Nos. 4,797,413, 4,847,289 and 4,731,368 disclose topically dosed thiophene sulfonamides which lower IOP by inhibiting carbonic anhydrase.

Thiophene bis-sulfonamides, which are carbonic anhydrase inhibitors useful for treating conditions attributable to a restriction of blood flow to the brain, including atherosclerosis, occlusion of blood vessels in the brain, stroke and other cerebro vascular diseases, are disclosed in the British Patent No. 1,516,024. Similar compounds are also disclosed in *Justus Liebigs Annalen der Chemie*, 1933, 501, 174-188 and in *Phosphorus Sulfur*, 1981, 10(1), 111-119.

Other thiophene bis-sulfonamides, which are carbonic anhydrase inhibitors useful as diuretics, are disclosed in the German Patent No. 1,096,916 and *Journal of Medicinal and Pharmaceutical Chemistry*, 1959, 1(6), 565-576.

The compounds of the present invention are new thiophene sulfonamides which are carbonic anhydrase inhibitors useful for lowering IOP without producing significant systemic side effects when delivered topically to the eye.

SUMMARY OF THE INVENTION

The present invention is directed to new thiophene sulfonamides which can be used to lower and control IOP. The compounds are formulated in pharmaceutical compositions for delivery.

The invention is also directed to methods for lowering and controlling IOP by the administration of the compositions comprising the thiophene sulfonamides of the present invention. The compositions can be administered systemically and/or topically to the eye.

DETAILED DESCRIPTION OF THE INVENTION

The thiophene sulfonamides of the present invention have the following structure.

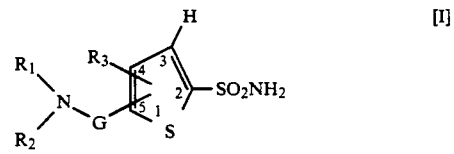

or a pharmaceutically acceptable salt thereof wherein:

$R_1$ is H; $C_{1-4}$ alkyl; $C_{2-4}$ alkyl substituted optionally with OH, halogen, $C_{1-4}$ alkoxy or $C(=O)R_7$.

$R_2$ is H; $C_{1-8}$ alkyl; $C_{2-8}$ alkyl substituted with OH, $NR_5R_6$, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or heteroaryl which can be unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0-2 and n is 0-2; $C_{2-4}$ alkoxy substituted optionally with $NR_5R_6$, halogen, $C_{1-4}$ alkoxy, or $C(=O)R_7$; phenyl, or heteroaryl, unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0-2 and n is 0-2; provided that $R_1$ and $R_2$ cannot both be H; or $R_1$ and $R_2$ can be joined to form a saturated ring of 5 or 6 atoms selected from O, S, C or N which can be unsubstituted or substituted optionally on carbon with OH, $NR_5R_6$, halogen, $C_{1-4}$ alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$ alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$.

$R_3$ is H; halogen; $C_{1-4}$ alkyl; $C_{1-8}$ alkoxy; $C_{1-8}$ alkylthiol; $C_{2-8}$ alkoxy substituted optionally with OH, $NR_5R_6$, halogen, $C_{1-4}$ alkoxy or $C(=O)R_7$; $C_{1-4}$ alkyl substituted optionally with $R_4$; or $R_1$ and $R_3$ can be joined together with carbon atoms to form a ring of from 5 to 7 members in which said carbon atoms can be unsubstituted or substituted optionally with $R_4$.

$R_4$ is OH; $C_{1-4}$ alkyl unsubstituted or substituted optionally with OH, $NR_5R_6$, halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$; $NR_5R_6$; phenyl, or heteroaryl, unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0-2 and n is 0-2;

provided that when $R_3$ is in the 4 position and is H or halogen then $R_1$ and $R_2$ are not H, $C_{1-6}$ alkyl substituted optionally with OH, $C_{1-6}$ alkoxy, $C_{2-6}$ alkoxycarbonyl, nor are they joined to form a 5, 6 or 7 member ring, saturated or unsaturated, comprised of atoms selected optionally from C, O, S, N in which said nitrogen, when saturated, is substituted optionally with H or $C_{1-6}$ alkyl or in which said carbon is substituted optionally with $C_{1-6}$ alkyl, $C_{1-6}$ alkoxy or OH; and when $R_3$ is in the 5 position and is H, Cl, Br, or $C_{1-3}$ alkyl then neither $R_1$ nor $R_2$ can be H or $C_{1-4}$ alkyl.

$R_5$ and $R_6$ are the same or different and are H; $C_{1-4}$ alkyl; $C_{2-4}$ alkyl substituted optionally with OH, halogen, $C_{1-4}$ alkoxy or $C(=O)R_7$; $C_{1-4}$ alkoxy; $C_{2-4}$ alkoxy substituted optionally with OH, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-2}$alkyl$C_{3-5}$cycloalkyl; or $R_5$ and $R_6$ can be joined to form a ring of 5 or 6 atoms selected from O, S, C or N which can be unsubstituted or substituted optionally on carbon with OH, (=O), halogen, $C_{1-4}$ alkoxy, $C(=O)R_7$, $C_{1-6}$ alkyl, $C_{1-6}$ alkyl substituted optionally with OH, halogen, $C_{1-4}$ alkoxy, $C(=O)R_7$ or on nitrogen with $C_{1-4}$ alkoxy, $C(=O)R_7$, $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$, wherein m is 0-2.

$R_7$ is $C_{1-8}$ alkyl; $C_{1-8}$ alkyl substituted optionally with OH, $NR_5R_6$, halogen, $C_{1-4}$ alkoxy or $C(=O)R_9$; $C_{1-4}$ alkoxy; $C_{2-4}$ alkoxy substituted optionally with OH, $NR_5R_6$, halogen or $C_{1-4}$ alkoxy; or $NR_5R_6$.

$R_8$ is $C_{1-4}$ alkyl; $C_{2-4}$ alkyl substituted optionally with OH, $NR_5R_6$, halogen, $C_{1-4}$ alkoxy or $C(=O)R_7$.

$R_9$ is $C_{1-4}$ alkyl; $C_{1-4}$ alkoxy; amino, $C_{1-3}$ alkylamino, or di-$C_{1-3}$ alkylamino; and G is $C(=O)$ or $SO_2$.

In the above definitions, the total number of carbon atoms in a substituent group is indicated by the $C_{i-j}$ prefix where i and j are numbers from 1 to 8 for example. This $C_{i-j}$ definition includes both the straight and branched chain isomers. For example, $C_{1-4}$ alkyl would designate methyl through the butyl isomers; and $C_{1-4}$ alkoxy would designate methoxy through the butoxy isomers.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different.

Structure [I] includes isomers, wherein $R_3$ and $GNR_1R_2$ are attached to the 4 and 5 position respectively or $R_3$ is attached to the 5 position and $GNR_1R_2$ is attached to the 4 position. Many of the novel compounds of Structure [I] posses one or more chiral centers and this invention includes all enantiomers, diastereomers and mixtures thereof.

SYNTHESIS

Compounds of the present invention can be prepared using a variety of procedures, a number of which are described below in equations 1 through 4.

Many of the novel compounds of Structure [I] can be prepared from N-t-Bu thiophene-2-sulfonamides with $R_3$ substituents according to the scheme shown in equation 1.

In general, N-t-Bu thiophene-2-sulfonamides can be metalated in the 5-position at low temperatures using a strong organometalic base such as n-butyllithium and condensed with sulfur dioxide gas to produce intermediate sulfinate salts (equation 1a). These intermediates can be readily oxidized to the corresponding sulfonyl chloride which in turn can be aminated with primary or secondary amines, bearing the requisite $R_1$ and $R_2$ substituents, to furnish the novel compounds of Structure [I] (equation 1b).

In many cases it is more advantageous to prepare initially simplified primary or secondary sulfonamides via the above sequence and then append the more complex $R_1$ and/or $R_2$ substituents using standard alkylation reactions (equation 1c). Primary sulfonamides can be prepared from the corresponding sulfonyl chloride by amination with ammonia or directly from sulfinate salts using hydroxylamine-O-sulfonic acid (equation 1d).

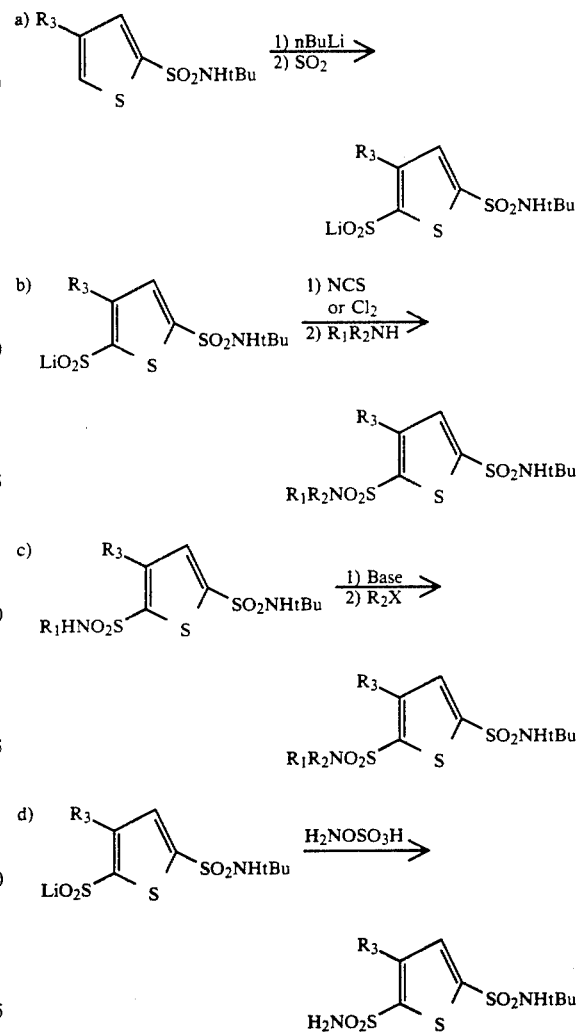

Equation 1

Many of the compounds of Structure [I] can be prepared using the procedures shown below in equation 2.

Equation 2

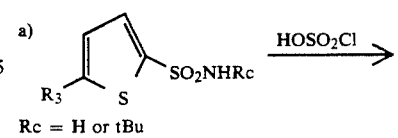

Rc = H or tBu

-continued
Equation 2

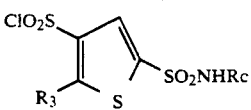

b) 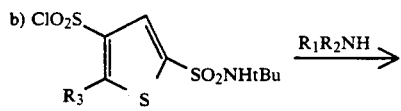

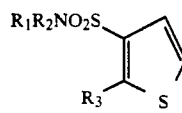 $\xrightarrow{R_1R_2NH}$

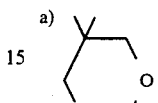

c) 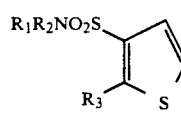 $\xrightarrow{\text{Equation 1c}}$

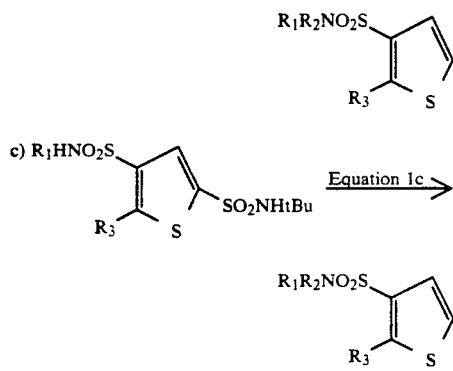

Chlorosulfination of thiophene 2-sulfonamides produce the 4-sulfonyl chlorides (equation 2a). These intermediate sulfonyl chlorides can be converted to the novel compounds of Structure [I] using the procedures (equations 2b and c) analogous to those described for equation 1.

Many of the novel compounds of Structure [I] can be prepared according the schemes shown below in equations 3 and 4.

Equation 3 a) 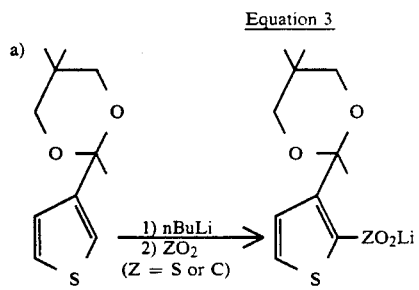

b) For Z = C

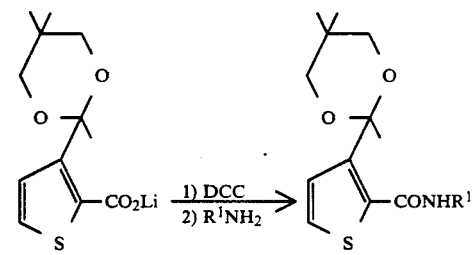

Ketals (equation 3a) can be metalated in the 2 position with a strong organometalic base such as n-butyllithium and condensed with $SO_2$ or $CO_2$ gas to furnish intermediate sulfinic acid or caboxylic acid salts in a way similar to that described in equation 1a. The sulfinic acid salts can be transformed into 2-sulfonamides derivatives via the two procedures outlined above in equations 1b and c. The carboxylic acid salts can be converted in a similar way as shown in equation 3b. The conversion of these acyclic sulfonamides and carboxamides into the desired cyclic compounds of Structure [I] can be accomplished using a variety of procedures well known in the art. Selected sequences are outlined in equations 4a, b and c.

Equation 4 a) 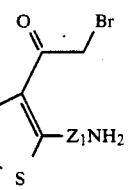

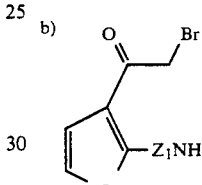 $\xrightarrow[\text{2) PBP}]{\text{1) } H_3O^+}$ 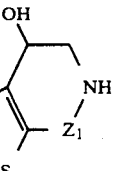

$Z_1 = SO_2$ or $CO$ b) 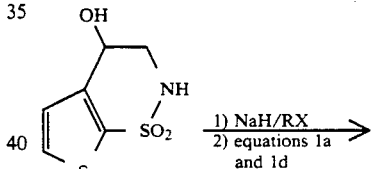 $\xrightarrow{NaBH_4}$ 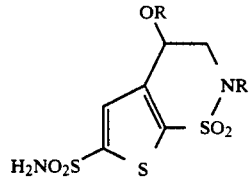

c) For $Z_1 = SO_2$

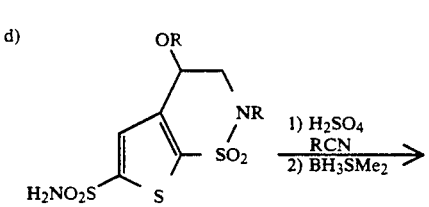 $\xrightarrow[\text{2) equations 1a and 1d}]{\text{1) NaH/RX}}$

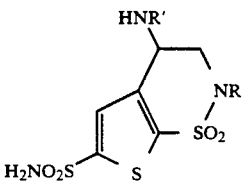

d)

$\xrightarrow[\text{2) } BH_3SMe_2]{\text{1) } H_2SO_4 \text{ RCN}}$ e) For $Z_1 = CO$

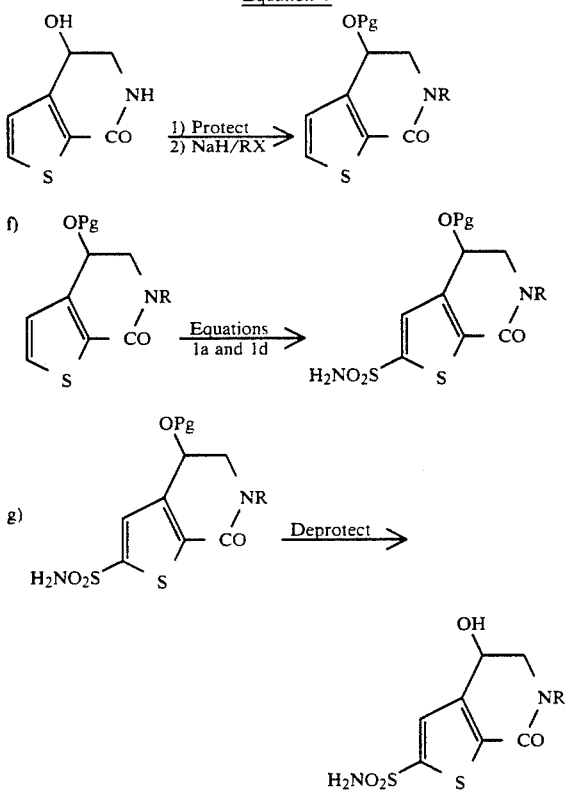

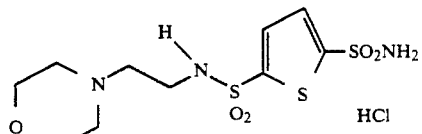

The compounds of Structure [I] can be incorporated into various types of ophthalmic formulations for delivery to the eye. These compounds may be combined with ophthalmologically acceptable preservatives, surfactants, viscosity enhancers, penetration enhancers, buffers, sodium chloride and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxypropylmethylcellulose, methylcellulose, polyvinylpyrrolidone, or the like to improve the retention of the medicament in the conjunctival sac.

The compounds are preferably formulated as topical ophthalmic solutions, with pH of about 4.5 to 7.5. The compounds will normally be contained in these formulations in an amount of 0.1% to 10% by weight, but preferably in an amount of 0.25% to 5.0% by weight. Thus, for topical presentation 1 to 3 drops of these formulations would be delivered to the surface of the eye 1 to 4 times a day according to the routine discretion of a skilled clinician.

The following examples, which are in no way limiting, illustrate the preparation of selected examples of the novel compounds of Structure [I]. The compound set forth in Examples 10 and 11 represents the preferred thiophene sulfonamide of this invention.

EXAMPLE 1

N-2-(4-morpholinyl)ethyl-2,5-thiophenedisulfonamide, Hydrochloride

Step A: N-(1,1-Dimethylethyl)-2-thiophenesulfonamide

To a solution of t-butylamine (8.35 g, 0.114 mol) in dry tetrahydrofuran (THF) (20 mL) cooled to 0° C. was added dropwise 2-thiophenesulfonyl chloride (5.0 g, 27.4 mmol). After the addition was completed, the reaction mixture was warmed to ambient temperature and stirred overnight. The mixture was extracted with ethyl acetate (3×80 mL) and the combined extracts were washed with water, dried over molecular sieves and concentrated. The residue was chromatographed on silica, eluting with 25% ethyl acetate-hexane, to yield 5.62 g (94%) of solid: mp 80°-82° C.

Step B: N-(1,1-Dimethylethyl)-2,5-thiophenedisulfonamide

To a solution of the product from Step A (1.5 g, 6.85 mmol) in THF (10 mL) cooled to −60° C. was added n-butyllithium in hexane (2.5M, 6.0 mL, 15.1 mmol). The mixture was stirred for 15 min at −60° C. and for 30 min at −10° C. Sulfur dioxide gas was passed through the surface of the mixture for 10 min. The cooling bath was removed and the mixture was stirred for an additional 1 h. The volatiles were evaporated and the residue was dissolved in water (30 mL) and sodium acetate trihydrate (5.59 g, 41.1 mmol) was added. The mixture was cooled in an ice-water bath and hydroxylamine-O-sulfonic acid (2.71 g, 23.9 mmol) was added. The cooling bath was removed and the mixture was stirred for 2 h. The suspension was extracted with ethylacetate (3×50 mL) and the combined extracts were washed with 5% sodium bicarbonate solution, brine and dried over molecular sieves. The solvent was evaporated and the residue was chromatographed on silica eluting with 40% ethylacetatehexane, to yield 1.25 g (61%) of a liquid which solidified on standing: mp 116°-120° C.

Step C: N-(1,1-Dimethylethyl)-N'-2-(4-morpholinyl)ethyl-2,5-thiophenedisulfonamide A solution of the product from Step B (1.05 g, 3.52 mmol), sodium hydride (60% dispersion in mineral oil, 310 mg, 7.75 mmol) and 4-(2-chloroethyl)morpholine hydrochloride (0.721 g, 3.88 mmol) in anhydrous dimethylformamide (DMF) (20 mL) was heated at 110° C. for 2.5 h and then stirred at ambient temperature overnight. The reaction mixture was extracted with ethylacetate (3×100 mL), washed with brine, dried over molecular sieves and concentrated. The residue was chromatographed on silica, elution with 50% ethylacetate-hexane, to yield 0.32 g (22%) of the desired product.

Step D:
N-2-(4-Morpholinyl)ethyl-2,5-thiophenedisulfonamide, Hydrochloride A solution of the product from Step C (0.31 g, 0.75 mmol) in trifluoroacetic acid (7 mL) was stirred at ambient temperature for 4 h. The trifluoroacetic acid was evaporated and the residue was chromatographed on silica, eluting with methylene chloridemethanol-ammonium hydroxide (10/1/0.1), to give 230 mg (86%) of a viscous liquid. The liquid was dissolved in ethanol and treated with ethanolic HCl. Evaporation gave a white solid which was recrystallized from ethanol-water to afford colorless crystals (145 mg, first crop): mp 219°-220° C.

Analysis calculated for $C_{10}H_{18}ClN_3O_5S_3$: C, 30.65; H, 4.63; N, 10.72 Found: C, 30.54; H, 4.67; N, 10.64.

EXAMPLE 2

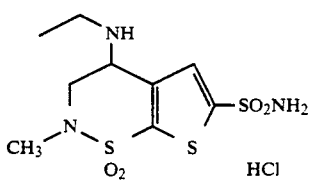

3,4-Dihydro-4-ethylamino-2-methyl-4H-thieno[3,2-e]-1,2-thiazine-6-sulfonamide-1,1-dioxide, Hydrochloride

Step A:
3-(2,5,5-Trimethyl-1,3-dioxane-2-yl)-thiophene-2-sulfonamide

To a solution of 3-(2,5,5-Trimethyl-1,3-dioxane-2-yl)thiophene (2.5 g, 11.7 mmol) in hexane (30 mL) cooled to 0° C. was added via syringe n-butyllithium in hexane (2.5M, 10.3 mL, 25.7 mmol) over 5 min. The mixture was stirred at 0° C. for 20 min, the ice bath was removed and the stirring was continued for 30 min. At this time a white precipitate formed. The mixture was cooled to −60° C. and THF (20 mL) was added. Sulfur dioxide was then passed through the surface of the mixture for 30 min. The mixture was warmed to ambient temperature and stirred for an additional 15 min. The volatiles were evaporated and to the residue was added water (50 mL) and sodium acetate trihydrate (9.55 g, 70.2 mmol). The solution was cooled on an ice bath and hydroxylamine-O-sulfonic acid (4.62 g, 40.9 mmol) was added. The mixture was stirred at ambient temperature for 1 h, extracted with ethylacetate (3×100 mL) and the combined extracts were washed with a sodium bicarbonate solution, brine and dried over molecular sieves. Evaporation to dryness gave a viscous liquid (4.93 g), which was chromatographed on silica eluting with 33% ethylacetate-hexane, to give a solid (2.47 g, 72%): mp 200°-202° C.

Step B: 3-Acetylthiophene-2-sulfonamide

A mixture of the compound from Step A (9.45 g, 32.5 mmol) and 1N HCl (100 mL) in THF (100 mL) was heated at reflux for 1 h. The THF was evaporated and the aqueous solution was made basic by the addition of sodium bicarbonate. The mixture was cooled using an ice bath and the precipatiate was filtered, washed with cold water and dried in vacuo to give 5.83 g (88%) of a solid: mp 193°-196° C.

Step C:
3,4-dihydro-4-hydroxy-4H-thieno[3,2-e]-1,2-thiazine-1,1-dioxide

The product from Step B (5.73 g, 28.0 mmol) was dissolved in hot THF (200 mL). The solution was cooled to 10° C. and pyridinium bromide perbromide (10.73 g, 33.5 mmol) was added. The mixture was allowed to stir at ambient temperature for 1 h. The volatiles were evaporated and the residue was mixed with water. The precipitate was filtered, washed with cold water and dried in vacuo overnight to give 7.77 g of a solid. A portion of this solid (3.49 g, 12.3 mmol) was suspended in ethanol (100 mL) and treated with sodium borohydride (266 mg, 7.04 mmol). The suspension turned clear after 10 min and was heated at reflux for 1 h. The ethanol was evaporated and the residue was extracted with ethylacetate, washed with brine and evaporated to give the product (1.80 g, 71%): mp 138°-140° C.

Step D:
3,4-Dihydro-2-methyl-4-methoxy-4H-thieno[3,2e]-1,2-thiazine-1,1-dioxide To a solution of the product from Step C (2.75 g, 13.4 mmol) in anhydrous DMF (40 mL) cooled to 0° C. was added sodium hydride (60% dispersion in mineral oil, 1.18 g, 29.5 mmol), followed by methyl iodide (2.5 mL, 40.2 mmol). The reaction mixture stirred at ambient temperature for 4 h and was poured onto ice and extracted with ethylacetate (3×80 mL). Evaporation gave 3.35 g of an orange liquid which was chromatographed on silica, eluting with 50% ethylacetate-hexane to give the desired product (2.42 g, 77%): mp 61°-63° C.

Step E:
3,4-Dihydro-2-methyl-4-methoxy-4H-thieno[3,2-e]-1,2-thiazine-6-sulfonamide-1,1-dioxide To a solution of the product from Step D (1.73 g, 7.42 mmol) in THF (15 mL) cooled to −60° C. was added via syringe n-butyllithium in hexane (2.5M, 3.56 mL, 8.91 mmol) over 5 min. After the addition was completed, the mixture was warmed to 0° C. and stirred for 20 min. The mixture was re-cooled to −60° C. and a stream of sulfur dioxide was passed through the surface of the mixture for 20 min. The mixture was warmed to ambient temperature and the volatiles were evaporated. To the residue was added sodium acetate trihydrate (3.03 g, 22.3 mmol) and water (50 mL) and the mixture was cooled to 0° C. Hydroxylamine-O-sulfonic acid (1.51 g, 13.4 mmol) was added and the mixture was allowed to stir for 30 min. The reaction mixture was extracted with ethylacetate (3×100 mL), dried over molecular sieves and concentrated to give an orange oil (2.25 g) which solidified on standing. The solid was crystallized from methanol-methylene chloride to give a colorless solid (1.21 g, 52%, first crop): mp 161°-162° C.

Step F:
3,4-Dihydro-2-methyl-4-acetamino-4H-thieno[3,2-e]-1,2-thiazine-6-sulfonamide-1,1-dioxide To sulfuric acid (5.0 g) cooled to 0° C. was added the product from Step E (1.10 g, 3.81 mmol) dissolved in acetonitrile (35 mL) dropwise over 10 min. The mixture was stirred at ambient temperature for 2.5 days and quenched by the addition of ice and ammonium hydroxide to adjust the pH to 10. The acetonitrile was evaporated and the white precipitate was filtered and dried to give 0.41 g of the desired product. The filtrate was extracted with ethylacetate. Evaporation to dryness gave an additional 0.33 g of the desired product (total yield 57%). Crystallization from methanol-methylene chloride gave colorless crystals: mp 252°–253° C.

Step G:
3,4-Dihydro-4-ethylamino-2-methyl-4H-thieno[3,2-e]-1,2-thiazine-6-sulfonamide-1,1-dioxide, Hydrochloride To a suspension of the product from Step F (0.95 g, 2.80 mmol) in anhydrous THF (70 mL) was added slowly a solution of boranedimethylsulfide complex in THF (2M, 4.9 mL, 9.8 mmol). The mixture was then heated at gentle reflux and the dimethyl sulfide was distilled out and condensed in a dry-ice cooled receiving flask. The solution was refluxed for an additional 2 h, cooled and concentrated HCl (10 mL) was added. The resulting mixture was heated at reflux for 30 min, cooled and poured into ice and sodium bicarbonate solution. The mixture was extracted with ethylacetate (3×100 mL) and the combined extracts were concentrated to give a viscous liquid, which was chromatographed on silica, eluting with 5% methanol-methylene chloride, to give a viscous oil (0.67 g, 74%). The oil was dissolved in ethanol (10 mL) and treated with ethanolic HCl. The volatiles were evaporated and the residue was crystallized from acetonitrile-ethanol and then from water: mp 141°–144° C.

Analysis Calculated for $C_9H_{16}ClN_3O_4S_3 \cdot H_2O$: C, 28.45; H, 4.78: N, 11.06. Found: C, 28.72; H, 4.54; N, 11.14.

EXAMPLE 3

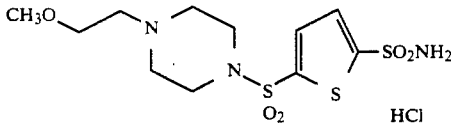

5-(4-[2-Methoxyethyl]piperazinylsulfonyl)thiophene-2-sulfonamide, Hydrochloride

Step A: 2-[4-(2-Methoxy)piperazinylfulfonyl]thiophene.

To a suspension of 1-(2-methoxyethyl)piperazine dihydrochloride (2.61 g, 12.0 mmol) in THF (100 mL) was added triethylamine (10 ML) and the resulting mixture was stirred for 10 min. Then a solution of 2-thiophenesulfonyl chloride (1.98 g, 10.84 mmol) was added in THF (3 mL) over 5 min. The reaction mixture was allowed to stir at room temperature for 1 h, the volatiles were evaporated and the residue was extracted with ethyl acetate (3×100 mL). The combined extracts were washed with a saturated sodium bicarbonate solution (50 mL), brine and dried over molecular sieves. Evaporation to dryness gave a viscous oil (2.09 g, 75%).

Step B:
5-(4-[2-Methoxyethyl]piperazinylsulfonyl)thiophene-2-sulfonamide, Hydrochloride To a solution of the compound from Step A (2.15 g, 7.41 mmol) in THF (15 mL) cooled to −78° C. was added slowly over 5 min n-butyllithium (2.5M, 3.86 mL, 9.64 mmol). The mixture was allowed to stir for 40 min when a stream of sulfur dioxide was passed through the surface of the mixture for 30 min. The mixture was warmed to ambient temperature, stirred for an additional 30 min and then evaporated to dryness. The residue was dissolved in water (30 mL) and sodium acetate trihydrate (3.03 g, 22.2 mmol) was added. The mixture was cooled to 0° C. and hydroxylamine-O-sulfonic acid (1.51 g, 13.3 mmol) was added. The mixture was stirred overnight, neutralized with saturated sodium bicarbonate solution and extracted with ethyl acetate (3×80 mL). The combined extracts were washed, dried and evaporated in a manner analogous to Step A to furnish a viscous liquid (2.17 g). This was chromatographed on silica (methylene chloride-methanol-ethyl acetate, 20/1/10) to give some recovered starting material (1.15 g, 53%) and the desired product (0.82 g, 30%). This product was treated with ethanolic HCl and crystallized from ethanol to furnish white crystals: mp 172°–173° C.

Analysis Calculated for $C_{11}H_{20}ClN_3O_5S_3$: C, 32.55; H, 4.97; N, 10.35. Found: C, 32.67; H, 4.92; N, 10.28.

EXAMPLE 4

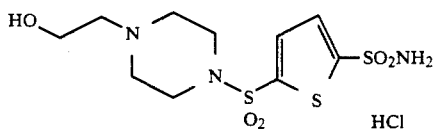

5(4-[2-Hydroxyethyl]piparazinylsulfonyl)thiophene-2-sulfonamide, Hydrochloride

To a solution of 2[4-(2-Hydroxyethyl)piparazinylsulfonyl]thiophene (2.5 g, 9.0 g mmol) in THF (15 mL) cooled to −78° C. was added slowly over 5 min n-butyllithium (2.5M, 8.5 mL, 20.8 mmol). The mixture was allowed to stir for 40 min at −65° C. and 20 min at −40° C. when a stream of sulfur dioxide was passed through the surface for 30 min. The mixture was warmed to ambient temperature, stirred for 1.5 h then evaporated to dryness. The residue was dissolved in water (30 mL) and sodium acetate trihydrate (6.16 g, 45.3 mmol) was added. The mixture was cooled to 0° C. and hydroxylamine-O-sulfonic acid (3.59 g, 31.7 mmol) was added. The mixture was stirred overnight, neutralized with saturated sodium bicarbonate solution and extracted with ethyl acetate (3×80 mL). The combined extracts were washed, dried and evaporated to furnish a viscous liquid (3.15 g). This was chromatographed on silica (methylene chloride-methanol 70/1) to give some recovered starting material (1.24 g, 50%) and the desired product as a liquid (0.8 g, 25%). The liquid was dissolved in ethanol, filtered and treated with ethanolic HCl. The mixture was filtered and the solid dried to give the desired product (0.54 g): mp 206°–207° C.

Analysis Calculated for $C_{10}H_{18}ClN_3O_5S_3$: C, 30.65; H, 4.65; N, 10.72. Found: C, 30.62; H, 4.64; N, 10.68.

EXAMPLE 5

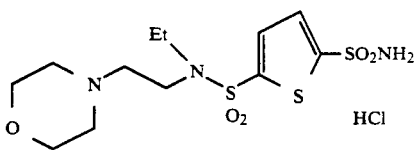

5-(4-Morpholinyl)ethylethylsulfamoylthiophene-2-sulfonamide, Hydrochloride

Step A: To a mixture of sodium hydride (60% dispersion in mineral oil, 0.606 g, 15.1 mmol) in N,N-dimethyl formamide (DMF) (60 mL) cooled to 0° C. was added 2-(4-morpholinyl)ethylsulfamoylthiophene (3.8 g, 13.8 mmol). The mixture was stirred for 1 h and then allowed to warm to ambient temperature overnight. The mixture was poured onto water, extracted with ethyl acetate, dried and concentrated to furnish a viscous oil (3.81 g). The liquid was dissolved in ethylacetate and washed with 1H NaOH, brine, dried and concentrated. This liquid was chromatographed on silica (ethyl acetate) to give the desired product as a liquid (2.95 g, 70%).

Step B:
5-(4-Morpholinyl)ethylethylsulfamoylthiophene-2-sulfonamide, Hydrochloride To a mixture of the product from Step A (2.2 g, 7.24 mmol) was treated sequentially with n-butyllithium, sulfur dioxide, hydroxylamine-O-sulfonic acid and ethanolic HCl in much the same was as described in example 4 to furnish the desired product as a hygroscopic white solid: mp 80°-85° C.

Analysis Calculated for $C_{12}H_{22}ClN_3O_5S_3$: C, 34.32; H, 5.28; N, 10.01. Found: C, 34.06; H, 5.20; N, 9.66.

EXAMPLE 6

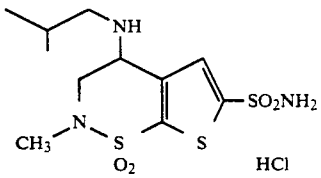

3,4-dihydro-2-methyl-4-(2-methyl)propylamino-4H-thieno[3,2-e]-1,2-thiazine-6-sulfonamide-1,1-dioxide, Hydrochloride Step A:
3,4-Dihydro-2-methyl-4H-thieno[3,2-e]-1,2-thiazine-4-ol-1,1-dioxide To a mixture of sodium hydride (60% dispersion in mineral oil, 1.352 g, 33.8 mmol) in DMF (60 mL) was added 2,3-dihydro-4-hydroxy-4H-thieno[2,3-e]-1,2-thiazine-1,1-dioxide (6.30 g, 30.7 mmol), prepared using the procedure described in Example 2. The mixture was cooled (dry ice-acetone bath) and methyl iodide (4.8 g, 33.8 mmol) was added over 5 min. After the addition was complete, the mixture was allowed to warm to ambient temperatures and stirred for 2 h. The mixture was then poured onto brine, extracted with ethylacetate (2×300 mL), dried and concentrated. The residue was chromatographed on silica (first with 50% ethylacetate/hexane and then with 75% ethylacetate/hexane) to give the desired product as a liquid (4.9 g, 73%).

Step B:
3,4-Dihydro-2-methyl-4-(2-methyl)propyl-4H-thieno[3,2-e]-1,2-thiazine-4-ol-1,1-dioxide The product from Step B (2.0 g, 9.13 mmol) was dissolved in methylene chloride (50 mL) containing triethylamine (TEA) (1.86 g, 18.3 mmol). The mixture was cooled to −30° C. and solution of tosyl chloride (3.48 g, 18.3 mmol) in methylene chloride (10 mL) was added dropwise over 5 min. The mixture was allowed to warm up to 0° C. gradually for 4.5 h, after which time isobutyl amine (5 mL) was added and the mixture was heated to 50° C. for 4 h and then stirred at ambient temperature overnight. The mixture was poured onto water, extracted with ethylacetate, dried and concentrated to give the crude product (5.1 g) as a viscous liquid. This liquid was chromatographed on silica (1/1 ethylacetate/hexane) to furnish the desired product (1.38 g, 55%) as a liquid.

Step C:
3,4-Dihydro-2-methyl-4-(2-methyl)propylamino-4H-thieno[3,2-e]-1,2-thiazine-6-sulfonamide-1,1-dioxide, Hydrochloride To a mixture of the product from Step B (1.29 g, 4.71 mmol) was treated sequentially with n-butyllithium, sulfur dioxide, hydroxylamine-O-sulfonic acid and ethanolic HCl in much the same was as described in Example 4 to furnish the desired product as a white solid: mp 141°-144° C.

Analysis Calculated for $C_{11}H_{20}ClN_3O_4S_3$–0.5$H_2O$: C, 33.12; H, 5.31; N, 10.53. Found: C, 33.16; H, 5.14; N, 10.49.

EXAMPLE 7

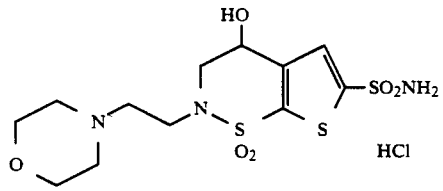

3,4-Dihydro-4-hydroxy-2-[2-(4-morpholino)ethyl]-4H-thieno[3,2-e]-1,2-thiazine-6-sulfonamide-1,1-dioxide, Hydrochloride Step A:
3,4-Dihydro-4-hydroxy-2-[2-(4-morpholino)ethyl]-4H-thieno[3,2-e]-1,2-thiazine-1,1-dioxide The selective alkylation of 2,3-dihydro-4-hydroxy-4H-thieno[2,3-e]-1,2-thiazine-1,1-dioxide (3.0 g, 14.6 mmol) with 2-chloroethyl morpholine (5.43 g, 29.2 mmol), using essentially the same procedure as described in Example 6, gave the desired product (2.25 g, 48%) as a viscous liquid.

Step B:
3,4-Dihydro-4-hydroxy-2-[2-(4-morpholino)ethyl]-4H-thieno[3,2-e]-1,2-thiazine-6-sulfonamide-1,1-dioxide, Hydrochloride The product from Step A (1.84 g, 5.79 mmol) was treated sequentially with n-butyllithium (2.2 equivalents), sulfur dioxide, hydroxylamine-O-sulfonic acid and methanolic HCl in much the same was as described in Example 4 to furnish the desired product as a white solid: mp 118°–125° C.

Analysis Calculated for $C_{12}H_{20}ClN_3O_6S_3$: C, 33.21; H, 4.65; N, 9.68. Found: C, 32.81; H, 4.31; N, 9.37.

EXAMPLE 8

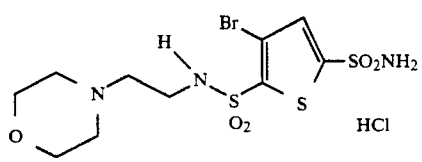

4-Bromo-5-[2-(4-morpholino)ethyl]-sulfamoylthiophene-2-sulfonamide, Hydrochloride Step A:
4-bromo-5-chlorosulfonyl-thiophene-2-sulfonamide To a stirring suspension of 4-bromo-5-phenylmethylthio-thiophene-2-sulfonamide (8.5 g, 23.0 mmol) in 1/1 acetic acid/water (70 mL) at 0° C. was passed chlorine gas for 1 h. The excess chlorine was flushed from the reaction mixture with a stream of nitrogen and the resultant solution was poured onto water (20 mL). The mixture was extracted with diethyl ether (3×40 mL) and the combined extracts were washed with water (2×20 mL), dried and concentrated to furnish the desired product (6.0 g, 76%) as a yellow oil.

Step B:
4-Bromo-5-[-2-(4-morpholino)ethyl]-sulfamoylthiophene-2-sulfonamide, Hydrochloride The product from Step A (2.3 g, 6.0 mmol) in THF (5 mL) was added dropwise to a cooled solution (0° C.) of triethylamine (1.5 g) and 4-(2-aminoethyl)-morpholine (1.95 g, 15 mmol) in THF (15 mL). The solution was stirred at 0° C. for 1 h and then was warmed to ambient temperature for an additional hour. The reaction mixture was concentrated, the residue was diluted with water and extracted with ethylacetate (3×50 mL). The combined extracts were washed with brine (10 mL), dried and concentrated to furnish the desired product as a white solid. The material was dissolved in ethanol and treated with ethanolic HCl and the resultant solid was isolated by filtration and dried. The desired product was obtained as a white solid: mp 180°–182° C.

Analysis Calculated for $C_{10}H_{17}BrClN_3O_5S_3$: C, 25.80; H, 3.67; N, 8.74. Found: C, 25.51; H, 3.64; N, 8.92.

EXAMPLE 9

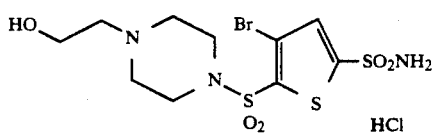

4-Bromo-5-[4-(2-hydroxyethyl)-piparazinylsulfamoyl]-thiophene-2-sulfonamide, Hydrochloride A sample of 4-bromo-5-chlorosulfonyl-thiophene-2-sulfonamide (5.2 g, 15.2 mmol) was treated sequentially with 1-(2-hydroxyethyl)-piperazine (4.97 g, 38.0 mmol) and ethanolic HCl in much the same way as described in Example 8 to furnish the desired hydrochloride salt.

This material was recrystallized from methanol to give a white solid: mp 212° C.

Analysis Calculated for $C_{10}H_{17}BrClN_3O_5S_3$—0.25-$H_2O$: C, 25.27; H, 3.71; N, 8.84. Found: C, 25.47; H, 3.51; N, 8.46.

EXAMPLE 10

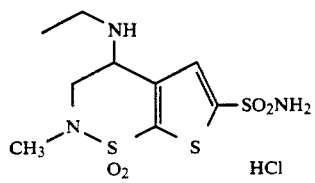

(+) 3,4-Dihydro-4-ethylamino-2-methyl-4H-thieno[3,2-e]-1,2-thiazine-6-sulfonamide-1,1-dioxide, Hydrochloride A hot solution (about 80° C.) of the free base corresponding to Example 2 (10.88 g, 33.5 mmol) in n-propanol (250 mL) was mixed with a hot solution of di-p-toluoyl-D-tartaric acid (3.27 g, 8.47 mmol) in n-propanol (250 mL). Activated carbon (2.0 g) was added and the mixture was kept at greater than 50° C. for 30 min and filtered through a pad of celite. The filtrate was concentrated to about 200 mL and was placed in the freezer overnight. The solid was filtered, washed with cold n-propanol and dried to give the tartrate salt (6.95 g), which was recrystallized four times from hot n-propanol (250, 200, 160 and 160 mL respectively) to afford the tartrate (4.30 g). The salt was mixed with a saturated sodium bicarbonate solution (300 mL) and the resulting suspension was allowed to stir for 1 h and was extracted with ethylacetate (3×300 mL). The extracts were dried, filtered and evaporated to dryness to afford the free base (2.71 g), which was treated with 2N HCl to give 2.71 g of the salt, $[\alpha]_D +14.7°$ C. (c=0.55, $H_2O$); m.p. 261°–263° C.

Analysis Calculated for $C_9H_{16}ClN_3O_4S_3$—0.5$H_2O$: C, 29.87; H, 4.46; N, 11.61. Found: C, 29.85; H, 4.28; N, 11.36.

EXAMPLE 11

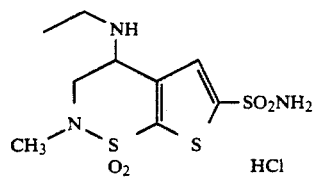

Alternative preparation of:
(+)-3,4-Dihydro-4-ethylamino-2-methyl-4H-thieno[3,2-e]-1,2-thiazine-6-sulfonamide-1,1-dioxide, Hydrochloride Step A: 3-(2,5,5-Trimethyl-1,3-dioxan-2-yl)thiophene Hydrogen chloride gas was bubbled briefly into a mixture of 3-acetylthiophene (100 g, 0.794 mol) and 2,2-dimethyl-1,3-propanediol (1.5 eq, 1.19 mol, 123 g) in toluene (650 mL) and the mixture was refluxed for 18 h with water removal using a Dean-Starck trap. Since only about half of the theoretical amount of water had been removed after this time, a few drops of concentrated sulfuric acid were added to the mixture and reflux was continued another 24 h. The mixture was allowed to cool to room temperature under a drying tube and potassium carbonate (10 g) was added followed by saturated aqueous sodium bicarbonate (300 mL) and hexane (1 L). The organic phase was separated and the aqueous was extracted with hexane (3×400 mL). The combined hexane extracts were washed with brine (6×500 mL), dried over MgSO4, treated with decolorizing carbon (Norite A), filtered through celite and evaporated under reduced pressure. The residue was distilled through a 12 inch Vigreux column to provide 120 g (71%) of the ketal as a colorless liquid that solidified on standing: bp 88° C./0.1 mmHg).

Step B: N-Methyl-3-acetyl-2-thiophenesulfonamide

A solution of the compound from Step A (50.0 g, 0.236 mol) in hexane (400 mL) was cooled to −60° C. under nitrogen. n-Butyllithium (1.3 eq, 120 mL of a 2.5M hexane solution) was added over 15 min while the temperature was maintained at −60° C. The cold bath was removed, and the reaction mixture was allowed to warm to room temperature, taking 30 min. After the mixture had stirred at room temperature for 30 min, it was again cooled to −60° C., at which point tetrahydrofuran (100 mL) was added. After the mixture had returned to −60° C., sulfur dioxide gas was bubbled into the reaction until the mixture was acidic, and the mixture was stirred overnight while warming to room temperature. N-Chlorosuccinimide (40 g, 1.3 eq) was added in one portion and stirring was continued at room temperature for 6 h. Methylamine gas was then bubbled into the mixture until the sulfonyl chloride was no longer present as indicated by TLC (silica gel, 30% ethyl acetate/hexane). The reaction mixture was then concentrated on the rotary evaporator under reduced pressure, and the residue was diluted with tetrahydrofuran (400 mL) and 1M aq. hydrochloric acid (400 mL) and refluxed for 1 h. The mixture was then cooled, basified using solid sodium bicarbonate, and partitioned between water (1 L) and ethyl acetate (500 mL). The organic phase was separated and the aqueous layer was further extracted with ethyl acetate (3×400 mL). The combined organic layers were washed with saturated aq. sodium bicarbonate (4×500 mL), dried over MgSO4, treated with decolorizing carbon (Norite A), filtered through celite, and concentrated. The residual oily solid was leached with diethyl ether (500 mL) resulting in a solid that was collected by filtration, washing with ether, to provide, after air drying, 31 g (60%) of the sulfonamide: mp 101°-103° C.

Step C:
N-Methyl-3-bromoacetyl-2-thiophenesulfonamide

A solution of the compound from Step B (71.0 g, 0.324 mol) in tetrahydrofuran (350 mL) was chilled in an ice-water bath to an internal temperature of 0°-5° C. Hydrogen chloride gas was bubbled into the solution very briefly, and then pyridinium bromide perbromide (0.9 eq, 0.291 mol, 93.0 g) was added in one portion. Within 10 min, a precipitate formed and the reaction turned orange-yellow. After 20 min, the reaction mixture was poured into ice-water (1 L), and the solid was collected by filtration, washing with water. The still moist solid was leached with ethanol (700 mL), filtered, washing first with ethanol (200 mL) and then diethyl ether (250 mL), and air dried on the funnel to provide 71 g (73%) of the bromo ketone: mp 112°-115° C.

Step D:
(+)-4-Hydroxy-2-methyl-2,3-dihydro-4H-thieno[3,2-e]-1,2-thiazine-1,1-dioxide A 5-L, jacketed flask fitted with a mechanical stirrer, a 1-L addition funnel, and a thermometer was charged with the compound from Step C (48.7 g, 0.163 mol) and tetrahydrofuran (3 L) under nitrogen, and the mixture was cooled to −25° C. with the aid of a refrigerated circulator. A solution of (+)-β-chlorodiisopinocampheylborane (2 eq, 0.326 mol, 105 g) in tetrahydrofuran (500 mL) was prepared in a separate flask and transferred into the addition funnel using a cannula. It was then added to the ketone solution at a rate such that the internal temperature did not exceed −24° C. (about 1 h was required). The reaction mixture was stirred at −25° C. for 7 h and then allowed to warm to room temperature before it was decanted into a 3-L flask. The tetrahydrofuran was removed on the rotary evaporator under reduced pressure and diethyl ether (1 L) was added to the pale yellow residue. Diethanolamine (2 eq, 34.2 g) was added, and the mixture was stirred with a mechanical stirrer for 2 h. The mixture was filtered through a sintered glass filter, and the white precipitate was collected and stirred with ether (250 mL). After filtration, the combined ether filtrates were concentrated on the rotary evaporator under reduced pressure. The residue was dissolved in 1:1 acetone/water (1 L), 1M aq. sodium hydroxide (30–40 mL) was added, and the solution was heated at 45° C. for 2 h. Removal of the acetone at 40 mmHg left an aqueous solution which was extracted with ethyl acetate (3×100 mL). The combined extracts were dried over Na2SO4, and the ethyl acetate was removed on the rotary evaporator under reduced pressure. The residue was taken up in acetonitrile (500 mL), and this solution was extracted with hexane (3×100 mL) before the acetonitrile was removed under reduced pressure. The residue was dissolved in 50% ethyl acetate/hexane and applied to a 1.5 L bed of 230–400 mesh silica gel in a 3-L sintered glass funnel. Elution first with 30% ethyl acetate/hexane (3 L) and then ethyl acetate (5 L) provided, after solvent removal, 32.8 g (92%) of the alcohol as a viscous orange oil that solidified on standing. The enantiomeric excess was determined to be 94% using a chiral chromatography method.

Step E:
(+)-4-Hydroxy-2-methyl-2,3-dihydro-4H-thieno[3,2-e]-1,2-thiazine-6-sulfonamide-1,1-dioxide A solution of the compound from Step D (53.3 g, 0.243 mol) in tetrahydrofuran (1.7 L) in a 3-L, 3-neck flask equipped with a mechanical stirrer, a 500 mL addition funnel, and a thermometer was cooled to −75° C. using a dry-ice/acetone bath. n-Butyllithium (2.2 eq, 0.535 mol, 215 mL of a 2.5M hexane solution) was added over about 30 min while the temperature was maintained below −72° C. The solution was allowed to warm to 0° C. for 2 h and then cooled again to −72° C. The addition funnel was replace with a gas inlet tube and sulfur dioxide gas was added as rapidly as possible until the pH remained below 6 for at least 1 minute. The mixture was allowed to warm to room temperature, decanted into a 3-L flask, and concentrated on the rotary evaporator under reduced pressure. The residue was dissolved in water (500 mL) and sodium acetate (59.8 g, 0.729 mol) was added, followed by hydroxylamine-O-sulfonic acid (49.5 g, 0.437 mol). The solution was stirred for 16 h at room temperature before the pH was adjusted to 7-8 by the cautious addition of solid sodium bicarbonate. The solution was extracted with ethyl acetate (3×100 mL) and the combined extracts were concentrated under reduced pressure. The residue was dissolved in 1M aq. sodium hydroxide (100 mL), and the solution was washed with ethyl acetate (3×50 mL), adjusted to pH 6-7 by the cautious addition of 6M aq. hydrochloric acid, and extracted with ethyl acetate (3×100 mL). The combined extracts were dried over $Na_2SO_4$ and concentrated under reduced pressure. The viscous oil that remained was dissolved in a minimum amount of warm ethyl acetate (<50 mL) and the product precipitated by the addition of methylene chloride (about 250 mL). This procedure was repeated twice on the concentrated mother liquor. The off-white solid collected by filtration from each of these operations was air dried and combined to provide 52.1 g (72%) of the sulfonamide: m.p. 168° C.

Step F:
(+)-3,4-Dihydro-4-ethylamino-2-methyl-4H-thieno[3,2-e]-1,2-thiazine-6-sulfonamide-1,1-dioxide Under nitrogen, a stirred solution of the compound from Step E (5.00 g, 16.8 mmol) and p-toluenesulfonyl chloride (1.1 eq, 18.5 mmol, 3.30 g) in tetrahydrofuran (100 mL) was treated with triethylamine (1.1 eq, 2.78 mL). After 18 h at room temperature, TLC indicated that starting material was still present so additional p-toluenesulfonyl chloride (0.4 eq, 1.3 g) and triethylamine (0.4 eq, 1.0 mL) was added. Stirring was continued for another 18 h, at which point TLC indicated the absence of starting material. Ethylamine (18 g) was added to the reaction mixture and the flask was stoppered. After 18 h at room temperature, TLC indicated that the intermediate tosylate was absent. At this point, the reaction mixture was combined with another 1.55 g run for workup. The mixture was partitioned between 1M aq. hydrochloric acid (100 mL) and diethyl ether (250 mL) and the acidic aqueous phase was separated. The organic phase was further extracted with 1M aq. hydrochloric acid (3×100 mL), and the combined aqueous layers were then back washed with ether (3×100 mL), basified using solid sodium bicarbonate, and extracted with ethyl acetate (4×250 mL). The combined organic ethyl acetate extracts were dried over $MgSO_4$, treated with decolorizing carbon (Norite A), filtered through celite, and concentrated under reduced pressure, to provide 5.2 g (73%) of the sulfonamide.

Step G:
(+)-3,4-Dihydro-4-ethylamino-2-methyl-4H-thieno[3,2-e]-1,2-thiazine-6-sulfonamide-1,1-dioxide The compound from Step F (27.0 g, 83.1 mmol) (94% ee) was dissolved in n-propanol (800 mL) and the solution was filtered through a sintered glass filter. The filtrate was heated to about 80° C., and an 80° C. solution of di-p-toluoyl-D-tartaric acid (15.7 g, 40.7 mmol) in n-propanol (500 mL) was added. The mixture was allowed to stand at room temperature overnight before it was cooled in an ice-water bath for 1 h. The crystals were collected by filtration, washed with cold n-propanol, and dried to provide 39.2 g (93%) of the di-p-toluoyl-D-tartrate salt of greater than 98% ee. Because this material was somewhat colored, it was recrystallized from n-propanol (1.5 L) to provide a first crop of 34.8 g. This solid was added to a saturated aqueous solution of sodium bicarbonate (500 mL), and the mixture was stirred for 1 h. The mixture was then extracted with ethyl acetate (4×400 mL), and the combined extracts were dried over 4 A molecular sieves, filtered, and concentrated on the rotary evaporator at reduced pressure to provide 20.2 g (75% recovery) of the (+)-sulfonamide of greater than 98% ee.

Step H:
(+)-3,4-Dihydro-4-ethylamino-2-methyl-4H-thieno[3,2-e]-1,2-thiazine-6-sulfonamide-1,1-dioxide, Hydrochloride The compound from Step G (20.2 g, 62.2 mmol) was treated with 2M ethanolic hydrogen chloride (40 mL), and then the mixture was evaporated to dryness under reduced pressure. The residue was dissolved in water (200 mL) and evaporated to dryness to provide the hydrochloride salt which was washed with ethyl acetate and dried under high vacuum at 78° C. for 6 h. The yield of the hydrochloride salt was 21.7 g (94%) as the hemihydrate.

Using the procedures described in equations 1 to 4, the Examples 1 to 11 and other well known procedures one skilled in the art can prepare the compounds listed in Tables 1 to 4.

In Tables 1 to 4 the following symbols correspond to the chemical structures: Me is $CH_3$; Et is $CH_2CH_3$; n-Pr is $CH_2CH_2CH_3$; i-Pr is $CH(CH_3)_2$; i-Bu is $CH_2CH(CH_3)_2$ and Ph is $C_6H_5$.

TABLE 1

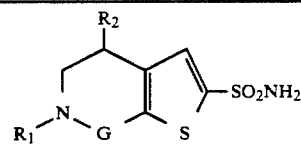

| G | $R_1$ | $R_2$ |
|---|---|---|
| $SO_2$ | H | HNMe |
| $SO_2$ | H | HNEt |
| $SO_2$ | Me | HNMe |
| $SO_2$ | Me | HNEt |
| $SO_2$ | Et | HNEt |
| $SO_2$ | n-Pr | HNEt |
| $SO_2$ | i-Pr | HNEt |
| $SO_2$ | $CH_2CHCH_2$ | HNEt |
| $SO_2$ | $CH_2CCH$ | HNEt |
| $SO_2$ | $(CH_2)_2OMe$ | HNEt |
| $SO_2$ | Me | $HNCH_2CHCH_2$ |

TABLE 1-continued

Structure: R2-CH-CH2-N(R1)-G-C=C(S)-SO2NH2 (thiophene ring with SO2NH2)

| G | R1 | R2 |
|---|---|---|
| SO2 | Me | HNC3H5 |
| SO2 | Me | HNCH2C3H5 |
| SO2 | Me | HNn-Pr |
| SO2 | Me | HNi-Bu |
| SO2 | Me | HN(CH2)3OH |
| SO2 | Me | HN(CH2)3OMe |
| SO2 | Me | OH |
| SO2 | Me | OMe |
| SO2 | Me | Oi-Bu |
| SO2 | Me | O(CH2)2N(CH2CH2)2O |
| SO2 | Me | O(CH2)2N(CH2CH2)2NCOMe |
| SO2 | Me | 4-Cl—Ph |
| SO2 | Me | 3-N(Me)2—Ph |
| SO2 | Me | 3-CH2N(CH2CH2)2O—Ph |
| SO2 | (CH2)2N(CH2CH2)2O | OMe |
| SO2 | (CH2)2N(CH2CH2)2O | OH |
| SO2 | (CH2)2N(CH2CH2)2O | OEt |
| SO2 | (CH2)2N(CH2CH2)2NCOMe | CH2OMe |
| SO2 | (CH2)2N(CH2CH2)2NCOMe | OEt |
| SO2 | (CH2)2N(CH2CH2)2O | CONHEt |
| SO2 | (CH2)5Me | HNEt |
| SO2 | (CH2)3OMe | HNEt |
| SO2 | CH2CONHMe | HNEt |
| SO2 | Ph | HNEt |
| SO2 | 4-Cl—Ph | HNEt |
| SO2 | 4-CONHMe—Ph | HNEt |
| SO2 | 4-SO2NMe2—Ph | HNEt |
| SO2 | 3-SO2Me—Ph | HNEt |
| SO2 | 4-OCF2H—Ph | HNEt |
| SO2 | 4-OMe—Ph | HNEt |
| SO2 | 4-OH, 3-CH2NMe2—Ph | HNEt |
| SO2 | 4-NHCOMe—Ph | HNEt |
| SO2 | CH2-4-pyridyl | HNEt |
| SO2 | (CH2)2OH | HNEt |
| SO2 | (CH2)2OEt | HNEt |
| SO2 | (CH2)2COMe | HNEt |
| SO2 | CH2CON(CH2CH2)2N(CH2)2OMe | OEt |
| SO2 | CH2CO2i-Pr | HNEt |
| SO2 | (CH2)2N(CH2CH2)2O | OCH2CH2OH |
| CO | H | HNMe |
| CO | H | HNEt |
| CO | Me | HNn-Pr |
| CO | Me | HNi-Bu |
| CO | Me | HN(CH2)2OH |
| CO | Me | HN(CH2)3OMe |
| CO | Me | OH |
| CO | Me | OMe |
| CO | Me | Oi-Bu |
| CO | Me | O(CH2)2N(CH2CH2)2O |
| CO | Me | O(CH2)2N(CH2CH2)2NCOMe |
| CO | Me | 4-Cl—Ph |
| CO | Me | 3-N(Me)2—Ph |
| CO | Me | 3-CH2N(CH2CH2)2O—Ph |
| CO | (CH2)2N(CH2CH2)2O | OMe |
| CO | (CH2)2N(CH2CH2)2O | OEt |
| CO | (CH2)2N(CH2CH2)2NCOMe | CH2OMe |
| CO | (CH2)2N(CH2CH2)2NCOMe | OEt |
| CO | (CH2)2N(CH2CH2)2O | CONHEt |
| CO | (CH2)5Me | HNEt |
| CO | (CH2)2OMe | HNEt |
| CO | CH2CONHMe | HNEt |
| CO | Ph | HNEt |
| CO | 4-Cl—Ph | HNEt |
| CO | 4-CONHMe—Ph | HNEt |
| CO | 4-SO2NMe2—Ph | HNEt |
| CO | 3-SO2Me—Ph | HNEt |
| CO | 4-OCF2H—Ph | HNEt |
| CO | 4-OMe—Ph | HNEt |
| CO | 4-OH, 3-CH2NMe2—Ph | HNEt |
| CO | 4-NHCOMe—Ph | HNEt |
| CO | (CH2)2OH | HNEt |
| CO | (CH2)2OEt | HNEt |
| CO | (CH2)2COMe | HNEt |

TABLE 1-continued

| G | R₁ | R₂ |
|---|---|---|
| CO | CH$_2$CON(CH$_2$CH$_2$)$_2$N(CH$_2$)$_2$OMe | OEt |
| CO | CH$_2$CO$_2$i-Pr | HNEt |
| CO | (CH$_2$)$_2$N(CH$_2$CH$_2$)$_2$O | OCH$_2$CH$_2$OH |

TABLE 2

| G | R₁ | R₂ |
|---|---|---|
| SO$_2$ | H | HNMe |
| SO$_2$ | H | HNEt |
| SO$_2$ | Me | HNn-Pr |
| SO$_2$ | Me | HNi-Bu |
| SO$_2$ | Me | HN(CH$_2$)$_2$OH |
| SO$_2$ | Me | HN(CH$_2$)$_3$OMe |
| SO$_2$ | Me | OH |
| SO$_2$ | Me | OMe |
| SO$_2$ | Me | Oi-Bu |
| SO$_2$ | Me | O(CH$_2$)$_2$N(CH$_2$CH$_2$)$_2$O |
| SO$_2$ | Me | O(CH$_2$)$_2$N(CH$_2$CH$_2$)$_2$NCOMe |
| SO$_2$ | Me | 4-Cl—Ph |
| SO$_2$ | Me | 3-N(Me)$_2$—Ph |
| SO$_2$ | Me | 3-CH$_2$N(CH$_2$CH$_2$)$_2$O—Ph |
| SO$_2$ | (CH$_2$)$_2$N(CH$_2$CH$_2$)$_2$O | OMe |
| SO$_2$ | (CH$_2$)$_2$N(CH$_2$CH$_2$)$_2$O | OEt |
| SO$_2$ | (CH$_2$)$_2$N(CH$_2$CH$_2$)$_2$NCOMe | CH$_2$OMe |
| SO$_2$ | (CH$_2$)$_2$N(CH$_2$CH$_2$)$_2$NCOMe | OEt |
| SO$_2$ | (CH$_2$)$_2$N(CH$_2$CH$_2$)$_2$O | CONHEt |
| SO$_2$ | (CH$_2$)$_5$Me | HNEt |
| SO$_2$ | (CH$_2$)$_2$OMe | HNEt |
| SO$_2$ | CH$_2$CONHMe | HNEt |
| SO$_2$ | Ph | HNEt |
| SO$_2$ | 4-Cl—Ph | HNEt |
| SO$_2$ | 4-CONHMe—Ph | HNEt |
| SO$_2$ | 4-SO$_2$NMe$_2$—Ph | HNEt |
| SO$_2$ | 3-SO$_2$Me—Ph | HNEt |
| SO$_2$ | 4-OCF$_2$H—Ph | HNEt |
| SO$_2$ | 4-OMe—Ph | HNEt |
| SO$_2$ | 4-OH, 3-CH$_2$NMe$_2$—Ph | HNEt |
| SO$_2$ | 4-NHCOMe—Ph | HNEt |
| SO$_2$ | (CH$_2$)$_2$OH | HNEt |
| SO$_2$ | (CH$_2$)$_2$OEt | HNEt |
| SO$_2$ | (CH$_2$)$_2$COMe | HNEt |
| SO$_2$ | CH$_2$CON(CH$_2$CH$_2$)$_2$N(CH$_2$)$_2$OMe | OEt |
| SO$_2$ | CH$_2$CO$_2$i-Pr | HNEt |
| SO$_2$ | (CH$_2$)$_2$N(CH$_2$CH$_2$)$_2$O | OCH$_2$CH$_2$OH |
| CO | H | HNMe |
| CO | H | HNEt |
| CO | Me | HNn-Pr |
| CO | Me | HNi-Bu |
| CO | Me | HN(CH$_2$)$_2$OH |
| CO | Me | HN(CH$_2$)$_3$OMe |
| CO | Me | OH |
| CO | Me | OMe |
| CO | Me | Oi-Bu |
| CO | Me | O(CH$_2$)$_2$N(CH$_2$CH$_2$)$_2$O |
| CO | Me | O(CH$_2$)$_2$N(CH$_2$CH$_2$)$_2$NCOMe |
| CO | Me | 4-Cl—Ph |
| CO | Me | 3-N(Me)$_2$—Ph |
| CO | Me | 3-CH$_2$N(CH$_2$CH$_2$)$_2$O—Ph |
| CO | (CH$_2$)$_2$N(CH$_2$CH$_2$)$_2$O | OMe |
| CO | (CH$_2$)$_2$N(CH$_2$CH$_2$)$_2$O | OEt |
| CO | (CH$_2$)$_2$N(CH$_2$CH$_2$)$_2$NCOMe | CH$_2$OMe |
| CO | (CH$_2$)$_2$N(CH$_2$CH$_2$)$_2$NCOMe | OEt |
| CO | (CH$_2$)$_2$N(CH$_2$CH$_2$)$_2$O | CONHEt |
| CO | (CH$_2$)$_5$Me | HNEt |

TABLE 2-continued

| G | $R_1$ | $R_2$ |
|---|---|---|
| CO | $(CH_2)_2OMe$ | HNEt |
| CO | $CH_2CONHMe$ | HNEt |
| CO | Ph | HNEt |
| CO | 4-Cl—Ph | HNEt |
| CO | 4-CONHMe—Ph | HNEt |
| CO | 4-$SO_2NMe_2$—Ph | HNEt |
| CO | 3-$SO_2Me$—Ph | HNEt |
| CO | 4-$OCF_2H$—Ph | HNEt |
| CO | 4-OMe—Ph | HNEt |
| CO | 4-OH, 3-$CH_2NMe_2$—Ph | HNEt |
| CO | 4-NHCOMe—Ph | HNEt |
| CO | $(CH_2)_2OH$ | HNEt |
| CO | $(CH_2)_2OEt$ | HNEt |
| CO | $(CH_2)_2COMe$ | HNEt |
| CO | $CH_2CON(CH_2CH_2)_2N(CH_2)_2OMe$ | OEt |
| CO | $CH_2CO_2i$-Pr | HNEt |
| CO | $(CH_2)_2N(CH_2CH_2)_2O$ | $OCH_2CH_2OH$ |

TABLE 3

| $R_1$ | $R_2$ | $R_3$ |
|---|---|---|
| $(CH_2)_2N(CH_2CH_2)_2O$ | H | H |
| $(CH_2)_2N(CH_2CH_2)_2O$ | H | H |
| $(CH_2)_2N(CH_2CH_2)_2O$ | Et | H |
| $(CH_2)_2N(CH_2CH_2)_2O$ | Me | H |
| $(CH_2)_2N(CH_2CH_2)_2O$ | Me | Me |
| $(CH_2)_2N(CH_2CH_2)_2O$ | H | Cl |
| $(CH_2)_2N(CH_2CH_2)_2O$ | H | Br |
| $(CH_2)_2N(CH_2CH_2)_2O$ | H | $CH_2OEt$ |
| $(CH_2)_2N(CH_2CH_2)_2O$ | H | $CH_2OMe$ |
| $(CH_2)_2N(CH_2CH_2)_2O$ | H | $CH_2Oi$-Pr |
| $(CH_2)_2N(CH_2CH_2)_2O$ | H | $CH_2Oi$-Bu |
| $(CH_2)_2N(CH_2CH_2)_2O$ | H | $CH_2OH$ |
| $(CH_2)_2N(CH_2CH_2)_2O$ | H | $CH(CH_3)OH$ |
| $(CH_2)_2N(CH_2CH_2)_2O$ | Me | $CH_2CONHEt$ |
| $(CH_2)_2N(CH_2CH_2)_2NCOMe$ | H | H |
| $(CH_2)_2N(CH_2CH_2)_2NCOMe$ | H | H |
| $(CH_2)_2N(CH_2CH_2)_2NCOMe$ | Me | H |
| $(CH_2)_2N(CH_2CH_2)_2NCOMe$ | Me | Me |
| $(CH_2)_2N(CH_2CH_2)_2NCOMe$ | H | Cl |
| $(CH_2)_2N(CH_2CH_2)_2NCOMe$ | H | Br |
| $(CH_2)_2N(CH_2CH_2)_2NCOMe$ | H | $CH_2OEt$ |
| $(CH_2)_2N(CH_2CH_2)_2NCOMe$ | H | $CH_2OMe$ |
| $(CH_2)_2N(CH_2CH_2)_2NCOMe$ | H | $CH_2Oi$-Pr |
| $(CH_2)_2N(CH_2CH_2)_2NCOMe$ | H | $CH_2Oi$-Bu |
| $(CH_2)_2N(CH_2CH_2)_2NCOMe$ | H | $CH_2OH$ |
| $(CH_2)_5Me$ | H | $CH_2N(CH_2CH_2)_2O$ |
| $(CH_2)_2OMe$ | H | $CH_2N(CH_2CH_2)_2O$ |
| $(CH_2)_2OH$ | H | $CH_2N(CH_2CH_2)_2O$ |
| $CH_2CONHMe$ | H | $CH_2N(CH_2CH_2)_2O$ |
| Ph | H | $CH_2N(CH_2CH_2)_2NCOMe$ |
| 4-Cl—Ph | H | Me |
| 4-CONHMe—Ph | H | Me |
| 4-$SO_2NMe_2$—Ph | H | Me |
| 3-$SO_2Me$—Ph | H | Me |
| 4-$OCF_2H$—Ph | H | Me |
| 4-OMe—Ph | Me | Me |
| 4-OH, 3-$CH_2NMe_2$—Ph | Me | Me |
| 4-NHCOMe—Ph | Me | Me |
| $(CH_2)_2OH$ | Me | Me |
| $(CH_2)_2OEt$ | Me | Me |
| $(CH_2)_2COMe$ | Me | Me |
| $CH_2CON(CH_2CH_2)_2N(CH_2)_2OMe$ | Me | H |
| $CH_2CO_2i$-Pr | Me | Me |
| $(CH_2)_2N(CH_2CH_2)_2O$ | H | $CH_2CH_2OH$ |

TABLE 3-continued

[Structure: R1R2N-SO2- attached to thiophene with R3 substituent and SO2NH2]

| R1 | R2 | R3 |
|---|---|---|
| (CH2)2N(CH2CH2)2NCOMe | H | CH2CH2OH |
| Me | Me | CH2NH(CH2)2OCH3 |
| Me | Me | CH2NH(CH2)3CF3 |
| CH2CHCH2 | H | CH2NH(CH2)2OCH3 |

| R1 and R2 | R3 |
|---|---|
| —(CH2CH2)2N(CH2)2OMe | H |
| —(CH2CH2)2N(CH2)2OMe | Me |
| —(CH2CH2)2N(CH2)2OH | H |
| —(CH2CH2)2N(CH2)2OH | Br |
| —(CH2CH2)2N(CH2)2OMe | Cl |
| —(CH2CH2)2N(CH2)2OMe | CH2OH |
| —(CH2CH2)2N(CH2)2OMe | CH2OMe |
| —(CH2CH2)2NCH2CONHMe | H |
| —(CH2CH2)2N(CH2)2CONHMe | H |

TABLE 4

[Structure: R2R1N-SO2- attached to thiophene with R3 substituent and SO2NH2]

| R1 | R2 | R3 |
|---|---|---|
| (CH2)2N(CH2CH2)2O | H | H |
| (CH2)2N(CH2CH2)2O | H | H |
| (CH2)2N(CH2CH2)2O | Me | H |
| (CH2)2N(CH2CH2)2O | Me | Me |
| (CH2)2N(CH2CH2)2O | H | Cl |
| (CH2)2N(CH2CH2)2O | H | Br |
| (CH2)2N(CH2CH2)2O | H | CH2OEt |
| (CH2)2N(CH2CH2)2O | H | CH2OMe |
| (CH2)2N(CH2CH2)2O | H | CH2Oi-Pr |
| (CH2)2N(CH2CH2)2O | H | CH2Oi-Bu |
| (CH2)2N(CH2CH2)2O | H | CH2OH |
| (CH2)2N(CH2CH2)2O | H | CH(CH3)OH |
| (CH2)2N(CH2CH2)2O | Me | CH2CONHEt |
| (CH2)2N(CH2CH2)2NCOMe | H | H |
| (CH2)2N(CH2CH2)2NCOMe | H | H |
| (CH2)2N(CH2CH2)2NCOMe | Me | H |
| (CH2)2N(CH2CH2)2NCOMe | Me | Me |
| (CH2)2N(CH2CH2)2NCOMe | H | Cl |
| (CH2)2N(CH2CH2)2NCOMe | H | Br |
| (CH2)2N(CH2CH2)2NCOMe | H | CH2OEt |
| (CH2)2N(CH2CH2)2NCOMe | H | CH2OMe |
| (CH2)2N(CH2CH2)2NCOMe | H | CH2Oi-Pr |
| (CH2)2N(CH2CH2)2NCOMe | H | CH2Oi-Bu |
| (CH2)2N(CH2CH2)2NCOMe | H | CH2OH |
| (CH2)5Me | H | CH2N(CH2CH2)2O |
| (CH2)2OMe | H | CH2N(CH2CH2)2O |
| (CH2)2OH | H | CH2N(CH2CH2)2O |
| CH2CONHMe | H | CH2N(CH2CH2)2O |
| Ph | H | CH2N(CH2CH2)2NCOMe |
| 4-Cl—Ph | H | Me |
| 4-CONHMe—Ph | H | Me |
| 4-SO2NMe2—Ph | H | Me |
| 3-SO2Me—Ph | H | Me |
| 4-OCF2H—Ph | H | Me |
| 4-OMe—Ph | Me | Me |
| 4-OH, 3-CH2NMe2—Ph | Me | Me |
| 4-NHCOMe—Ph | Me | Me |
| (CH2)2OH | Me | Me |
| (CH2)2OEt | Me | Me |
| (CH2)2COMe | Me | Me |
| CH2CON(CH2CH2)2N(CH2)2OMe | Me | H |
| CH2CO2i-Pr | Me | Me |
| (CH2)2N(CH2CH2)2O | H | CH2CH2OH |
| (CH2)2N(CH2CH2)2NCOMe | H | CH2CH2OH |

| R1 and R2 | R3 |
|---|---|
| —(CH2CH2)2N(CH2)2OMe | H |
| —(CH2CH2)2N(CH2)2OMe | Me |
| —(CH2CH2)2N(CH2)2OMe | Cl |

TABLE 4-continued

[Structure: R₂R₁N-S(O₂)-... R₃... -SO₂NH₂ on thiophene ring]

| | |
|---|---|
| —(CH₂CH₂)₂N(CH₂)₂OMe | CH₂OH |
| —(CH₂CH₂)₂N(CH₂)₂OMe | CH₂OMe |
| —(CH₂CH₂)₂NCH₂CONHMe | H |
| —(CH₂CH₂)₂N(CH₂)₂CONHMe | H |

The following examples are representative ophthalmic formulations including the thiophene sulfonamides of the present invention. The formulations can be administered topically to the eye 1 to 3 drops 1 to 4 times per day according to the discretion of a skilled clinician.

EXAMPLE 12

Ophthalmic Suspension

| Ingredient | Concentration (wt %) |
|---|---|
| 3,4-Dihydro-4-methoxy-2-methyl-4H-thieno[3,2-e]-1,2-thiazine- 6-sulfonamide-1,1-dioxide (Compound) | 3.0% |
| Hydroxypropylmethylcellulose | 0.5% |
| Dibasic Sodium Phosphate | 0.2% |
| Disodium Edetate | 0.01% |
| Sodium Chloride | 0.8% |
| Purified Water | q.s |
| Benzalkonium Chloride | 0.01% |
| Polysorbate 80 | 0.1% |
| NaOH/HCl | pH 7.02 |

The Compound (0.09 g), benzalkonium chloride (0.03 g), polysorbate 80 (0.15 g) can be mixed together in water (1.23 g) and ball milled for approximately 4 h. A hydroxypropylmethylcellulose vehicle can be prepared by mixing 2% aqueous sodium chloride (1.28 g) and water (35 g) together and the pH adjusted to 7.4 by the addition of 1N HCl (250 μL). A portion of this vehicle (1.5 mL) can be added to the mixture containing the Compound to furnish the desired suspension.

EXAMPLE 13

Ophthalmic Solution

| Ingredient | Concentration (wt %) |
|---|---|
| 3,4-Dihydro-4-ethylamino-2-methyl-4H-thieno[3,2-e]-1,2-thiazine- 6-sulfonamide-1,1-dioxide, Hydrochloride (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) were mixed together in water (1.44 g) and the pH of the solution was adjusted to 5.02 by the addition of 1N NaOH (10 μL). The hydroxyethylcellulose vehicle was prepared by mixing together monobasic sodium phosphate (0.26 g), dibasic sodium phosphate (0.02 g) and disodium edetate (0.02 g) in water (96.7 g). The benzalkonium chloride (2.0 g) and hydroxyethylcellulose were added to the mixture and the pH was adjusted to 5.01 by the addition of 1N HCl (100 μl). A portion of this vehicle (1.5 g) was added to the solution containing the compound and the pH was adjusted to 5.03 by the addition of 1N NaOH (10 μL).

EXAMPLE 14

Ophthalmic Gel

| Ingredient | Concentration (wt %) |
|---|---|
| 3,4-Dihydro-2-methyl-4-(2-methyl)propylamino-4H-thieno[3,2-e]-1,2-thiazine- 6-sulfonamide-1,1-dioxide, Hydrochloride | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 mL), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

EXAMPLE 15

Ophthalmic Solution

| Ingredient | Concentration (wt %) |
|---|---|
| (+)-3,4-Dihydro-4-ethylamino-2-methyl-4H-thieno[3,2-e]-1,2-thiazine- 6-sulfonamide-1,1-dioxide, Hydrochloride (Compound) | 2.27% |
| Hydroxypropylmethylcellulose | 3.3% |
| Sodium Acetate Dihydrate | 0.1% |
| Mannitol (Osmolality = 282 mOsm) | 2.44% |
| Benzalkonium Chloride | 0.01% |
| Disodium Edetate | 0.01% |
| Purified Water | q.s. |
| HCl/NaOH | pH 5.0 |

The sodium acetate (0.2 g), disodium edta (0.02 g), benzylalkonium chloride (2.1 g of a 1% solution) and mannitol (5.32 g) were dissolved in water for injection (115 mL). The pH was adjusted to 5.0 with 1N sodium hydroxide and the final volume was adjusted to 117 mL with water for injection. Hydroxypropylmethylcellulose (83.0 g of an 8% solution) was mixed with the 117 mL of the acetate buffer solution to furnish the vehicle. To prepare the final formulation, 0.068 g of the Compound was diluted with vehicle to make 3.0 mL total volume and the pH was adjusted to 5.0 with 1N sodium hydroxide (5 μL).

We claim:

1. A compound selected from the group consisting of: 3,4-Dihydro-2-methyl-4-(2-methyl)propylamino-4H-thieno[3,2-e]-1,2-thiazine-6-sulfonamide-1,1-dioxide; 3,4-Dihydro-4-methoxy-2-[2-(4-morpholino)ethyl]-4H-thieno[3,2-e]-1,2-thiazine-6-sulfonamide-1,1-dioxide, 3,4-Dihydro-4-ethylamino-2-methyl-4H-thieno[3,2-e]-1,2-thiazine-6-sulfonamide-1,1-dioxide;

3,4-Dihydro-4-ethylamino-2-allyl-4H-thieno[3,2-e]-1,2-thiazine-6-sulfonamide-1,1-dioxide;

3,4-Dihydro-4-ethylamino-2-n-propyl-4H-thieno[3,2-e]-1,2-thiazine-6-sulfonamide-1,1-dioxide;

3,4-Dihydro-4-ethylamino-2-(2-methoxyethyl)-4H-thieno[3,2-e]-1,2-thiazine-6-sulfonamide-1,1-dioxide; and 3,4-Dihydro-4-hydroxy-2-[2-(4-morpholino)ethyl]-4H-thieno[3,2-e]-1,2-thiazine-6-sulfonamide-1,1-dioxide.

2. The compound of claim 1 which is 3,4-Dihydro-4-ethylamino-2-methyl-4H-thieno[3,2-e]-1,2-thiazine-6-sulfonamide-1,1-dioxide.

3. (+)-3,4-Dihydro-4-ethylamino-2-methyl-4H-thieno[3,2-e]-1,2-thiazine-6-sulfonamide-1,1-dioxide.

4. A formulation for controlling intraocular pressure comprising a therapeutically effective amount of the compound of claim 1 in a pharmaceutically acceptable carrier.

5. The formulation of claim 4 wherein the compound concentration is between about 0.1 and 10% by weight.

6. A formulation for controlling intraocular pressure comprising a therapeutically effective amount of the compound of claim 3 in a pharmaceutically acceptable carrier.

7. The formulation of claim 6 wherein the compound concentration is between about 0.1 and 10% by weight.

8. A method for controlling intraocular pressure which comprises topically administering to the affected eye a therapeutically effective amount of the compound of claim 1.

9. A method for controlling intraocular pressure which comprises topically administering to the affected eye a therapeutically effective amount of the compound of claim 3.

10. A method for controlling intraocular pressure which comprises topically administering the formulation of claim 1.

11. A formulation for controlling intraocular pressure, comprising between about 0.25 wt % and 5.0 wt % (+)-3,4-Dihydro-4-ethylamino-2-methyl-4H-thieno[3,2-e]-1,2-thiazine-6-sulfonamide-1,1-dioxide in a pharmaceutically acceptable carrier.

* * * * *